United States Patent [19]

Mascher et al.

[11] 4,070,154

[45] Jan. 24, 1978

[54] METHOD AND APPARATUS FOR DETERMINING THE ALCOHOL CONTENT OF FUELS

[76] Inventors: Werner Mascher, Bismarckstr. 6, 1000 Berlin 41; Wolfgang Kretschmer, Kaiserdamm 15, 1000 Berlin 19; Gerhard Schmidt, Wesserstr. 155/156, 1000 Berlin 44, all of Germany

[21] Appl. No.: 769,023

[22] Filed: Feb. 16, 1977

[30] Foreign Application Priority Data

Feb. 27, 1976 Germany .............................. 2608062

[51] Int. Cl.$^2$ ...................... G01N 31/22; G01N 33/22
[52] U.S. Cl. .................................... 23/230 R; 252/408
[58] Field of Search ....................... 23/230 R; 252/408

[56] References Cited

U.S. PATENT DOCUMENTS

| 1,689,901 | 10/1978 | Williams .............................. 23/230 R |
| 2,209,764 | 7/1946 | Cassen et al. .................... 23/230 R X |
| 3,810,737 | 5/1974 | Geist et al. ........................... 23/230 R |

FOREIGN PATENT DOCUMENTS 2,261,200  1/1974  Germany ............................ 23/230 R

*Primary Examiner*—Robert M. Reese
*Attorney, Agent, or Firm*—Mark P. Stone; Haynes N. Johnson

[57] ABSTRACT

A convenient, useful and efficient method and apparatus for determining the amount of alcohol contained in fuels. It is particularly useful for measuring the alcohol content of jet fuel, and is practiced by mixing a known amount of the fuel to be measured with a known amount of emulsion, the emulsion comprising a known amount of 8-Hydroxyquinoline ester of the O-vanadic acid. A resulting reaction causes a portion of the mixture to discolor, the amount of discoloration indicating the alcohol content of the fuel. This process can be performed in an apparatus comprising a tube with all of the necessary chemicals pre-mixed, thereby only requiring the addition of the fuel to be tested. Such an apparatus can be prepared in advance, sealed, and stored for a period of up to 2 years.

9 Claims, No Drawings

METHOD AND APPARATUS FOR DETERMINING THE ALCOHOL CONTENT OF FUELS

BACKGROUND OF THE INVENTION AND DISCUSSION OF THE PRIOR ART

In order to assure the safe operation of jet aircraft, a variety of alcohols are being added to the fuel for the purpose of preventing formation of ice particles caused by the freezing of traces of water which may be present in the fuel. As an example of this, ethyleneglycolomethylether may be added to the jet fuel in quantities of one tenth to fifteen hundredths of a percent by volume, for the purpose of inhibiting the formation of ice. Because of the relationship between the addition of ice inhibitors to the fuel and the safety of the flight of the aircraft, there has been a long felt need for an easy to employ method to determine accurately and instantaneously the quantity of alcohol in jet fuel.

One method of testing jet fuel for alcohol content known to the art is described in West German Patent No. DT-PS-2,261,200. This method uses a small testing tube. The dimensions of the tube used are chosen so that the time of reaction of the chemical indicator can be determined in advance. This procedure has been known to the art and is commonly employed in column type chromotography. An emulsion matrix is formed, for example, by saturating a fine grained gel (with grain sizes preferably between three tenths and five tenths of a millimeter) with sodium monovanadiate and then drying it. Subsequent to this, water is added to the mixture to provide a certain level of moisture content. This emulsion matrix is then poured into the small tube and can be stored for long periods of time. An organic acid such as acetic acid can be added to the mixture at this time or alternately added to the mixture just prior to the testing of the jet fuel.

A solution of 8-Hydroxyquinoline in benzine or in any other appropriate organic solvent which is free of OH-group chemicals, must be available in certain pre-measured quantities at the time of the testing of the fuel. Immediately before the testing, the 8-Hydroxyquinoline solution must be poured into the tube, thereby causing a portion of the emulsion matrix, which was already present in the tube, to become green in color. At this point the fuel to be tested is passed through the small tube, which is open at both ends. This causes a certain amount of the emulsion matrix to become discolored. The proportion of the matrix which becomes discolored is directly related to the alcohol content of the fuel. At a higher alcohol content level, more of the matrix becomes discolored than at a lower alcohol content level. Thus, the alcohol content of the jet fuel tested can be determined.

One notable disadvantage of the above described method is that it is awkward. Immediately prior to the testing of the fuel, a separate reactant in a specified concentration and quantity first must be poured into the tube before the fuel can be tested. Because of the encumbrance associated with this method, the possibility of making mistakes and errors is enhanced.

Another critical disadvantage of the above stated prior art method is that when the 8-Hydroxyquinoline is added to the tube just prior to the testing of the fuel, only the upper portion of the emulsion matrix in the tube becomes green colored. The remainder of the emulsion matrix will take on a green color only when the fuel to be tested is added. Subsequent to this reaction, a portion of the now entirely green emulsion matrix will discolor, the amount of discoloration indicating the alcohol content of the fuel. Because of this two phase reaction, there is a distinct possibility that the observer will draw the wrong conclusion that the alcohol content in the fuel causes the entire emulsion matrix to become discolored when, in reality, it is the 8-Hydroxyquinoline which causes the entire emulsion matrix to take on a greenish color and the alcohol content in the fuel is only responsible for causing the greenish colored emulsion matrix to take on a different color.

The present invention, to be disclosed and described as follows, overcomes the problems and disadvantages that are associated with the prior art method and provides a simple and easy to use method and apparatus that eliminates the necessity of having to add any chemicals to the tube in pre-measured quantities just prior to the testing of the jet fuel, and provides more accurate results than were obtained with the prior art method.

SUMMARY OF THE INVENTION

This invention provides an accurate, simple, convenient and easy to use method and apparatus for determining the alcohol content of jet fuel, or any other fuels, eliminating the sources and causes for error found in the prior art method.

An emulsion material, which comprises a gel of finely grained particles, is saturated with a solution of sodium-vanadiate, 8-Hydroxyquinoline, water, acetic acid and an organic solvent which is free of OH-group chemicals and insoluble in water. The resultant combination can then be stored in a small tube.

The invention can be practiced in two steps. The first step comprises saturating the emulsion material with watery sodiumvanadiate solution and then drying the resulting first mixture until it comprises a moisture content of about 10% to 15% by volume. The second step comprises adding a solution of acetic acid and 8-Hydroxyquinoline in an organic solvent containing no OH-group chemicals to the first mixture.

The advantage of having all of the chemicals necessary for the testing of the fuel together in one tube in advance of the time of the test, is that all that is required to perform the test is the addition of the fuel to be tested to the tube. Therefore, unlike using the method known to the prior art which awkwardly required the addition of a pre-measured quantity of 8-Hydroxyquinoline immediately prior to the test, the present invention may be practiced more easily and efficiently. Additionally, the possibility of confusion and mistake by the observer that exists in the prior art method, as was previously explained, is eliminated by the invention because at the time the fuel to be tested is added, the entire solution in the tube is of a bluish-green color.

By pre-mixing all of the chemicals necessary for the test in a small tube in advance of the test, as was described above, the entire mixture displays a uniform bluish-green coloring. Upon adding a pre-determined amount of the fuel to be tested to the tube, a portion of the bluish-green mixture becomes discolored. The ratio of the amount of mixture that is discolored by the fuel, as compared to the amount of mixture that is not caused to be discolored by the fuel, indicates the alcohol content of the fuel. The amount of discoloration, and therefore the measurement of the alcohol content of the fuel, can now be calculated by observing the tube and noting the relative amount of discoloration of the mixture caused by the addition of the fuel.

DESCRIPTION OF THE PREFERRED EMBODIMENTS 100 grams of grainy gel of medium porosity, comprising grains within a size range of approximately 0.2 to 0.3 millimeters, is saturated with a solution of approximately 50 to 70 milliliters of sodiumvanadiate and de-ionized water, the concentration of the sodiumvanadiate solution having a sufficient amount of sodiumvanadiate to cause the resulting mixture to comprise between 80 to 120 milligrams of sodiumorthovanadiate. (The invention can be best practiced if the resulting mixture comprises 100 to 110 milligrams of sodiumorthovanadiate).

Then, the mixture is dried completely. Subsequent to this, de-ionized water is added in sufficient quantity to raise the moisture content of the mixture to about 10% to 15% of the volume of the mixture. (The invention can be best practiced if the moisture content is about 10% of the volume of the mixture).

Subsequent to this, a 100 milliliter solution is prepared by dissolving about 150 to 250 milligrams of 8-Hydroxyquinoline in about 95 to 99 milliliters of toluol and adding to this about 1 to 5 milliliters of glacial acetic acid. (This invention is best practiced if this 100 milliliter solution contains about 180 to 200 milligrams of 8-Hydroxyquinoline dissolved in 98 milliliters of toluol and 2 milliliters of glacial acetic acid).

Now, about 50 to 70 milliliters of the above described 100 milliliter 8-Hydroxyquinoline solution is added to the previously prepared sodiumorthovanadiate mixture.

This resulting combination is then thoroughly homogenized, poured into small tubes and sealed. The tubes containing the resulting combination can be stored for periods of up to two years.

The above illustration is only an example of the invention and is not intended to limit its scope. The invention is meant to include all modifications and variations of the above disclosure that fall within the claims and spirit of the invention.

We claim:

1. A method for determining the alcohol content of fuels from a chemical color reaction comprising the steps of:
    a. preparing a first mixture by saturating an emulsion material with sodiumvanadiate and water;
    b. preparing a second mixture which is uniform in color by adding a solution of 8-Hydroxyquinoline, acetic acid and an organic solvent which is insoluble in water and free of OH-group chemicals to said first mixture; and
    c. adding the fuel to be tested to said second mixture, thereby causing a discoloration of a portion of said second mixture indicating the alcohol content of said fuel.

2. A method as recited in claim 1 further comprising the steps of:
    d. observing the extent of the discoloration of said second mixture; and
    e. calculating the alcohol content of said fuel from said observation.

3. A method as recited in claim 1 wherein 40 to 70 milliliters of said solution of 8-Hydroxyquinoline, acetic acid and organic solvent is added to said first mixture for each 100 grams of emulsion material contained in said first mixture.

4. A method as recited in claim 1 wherein said emulsion material comprises a grained gel, the size of the grained particles being in the range of 0.3 to 0.5 millimeters.

5. A method as recited in claim 1 wherein said first and second mixtures are prepared inside of a small tube.

6. A method as recited in claim 1 wherein the amount of water added to said first mixture is sufficient to raise the water content of said first mixture to 10 to 15 percent of its volume.

7. A method as recited in claim 1 further comprising the step of drying said first mixture to reduce the water content of said first mixture to 10 to 15 percent of its volume before preparing said second mixture.

8. A method as recited in claim 1 wherein said second mixture comprises 80 to 120 milligrams of sodiumorthovanadiate and 150 to 250 milligrams of 8-Hydroxyquinoline dissolved in 95 to 99 milliliters of toluol and 1 to 5 milliliters of acetic acid.

9. A method as recited in claim 1 wherein said second mixture is stored for a time period of up to 2 years before the fuel to be tested is added.

* * * * *